United States Patent [19]

Wagner

[11] Patent Number: 4,997,825

[45] Date of Patent: Mar. 5, 1991

[54] SYNERGISTIC TREATMENT METHOD

[75] Inventor: Jack F. Wagner, Greenfield, Ind.

[73] Assignee: Eli Lilly and Company, Indianapolis, Ind.

[21] Appl. No.: 424,787

[22] Filed: Oct. 20, 1989

Related U.S. Application Data

[63] Continuation of Ser. No. 945,114, Dec. 22, 1986, abandoned.

[51] Int. Cl.[5] ...................... A61K 31/56; A61K 37/00
[52] U.S. Cl. ....................................... 514/171; 514/12; 514/13
[58] Field of Search ............................ 514/12, 13, 171

[56] References Cited

U.S. PATENT DOCUMENTS 4,670,249  6/1987  Ivy et al. ............................ 514/450

FOREIGN PATENT DOCUMENTS 1788221  6/1985  Canada ................................. 514/12
2238476  2/1975  France .
2240718  3/1975  France .

OTHER PUBLICATIONS

Chemical Abstracts (83:136918b) 1975.
*Journal of Endocrinology*, vol. 104, No. supplement, Mar. 1985, p. 45; C. A. Edwards et al.: "Interactions between GRF and Other Neuroregulators of GH Secretion" (abstract).

*Primary Examiner*—Stanley J. Friedman
*Assistant Examiner*—Kevin Weddington
*Attorney, Agent, or Firm*—Kathleen R. S. Page; Leroy Whitaker

[57]  ABSTRACT

The concentration of endogenous growth hormone in the bloodstream of an economic mammal is increased by the simultaneous administration of an estrogen and a growth hormone releasing factor.

15 Claims, No Drawings

SYNERGISTIC TREATMENT METHOD

This application is a continuation of application Ser. No. 945,114, filed Dec. 22, 1986, now abandoned.

FIELD OF THE INVENTION

This invention belongs to the fields of animal husbandry and biochemistry, and provides an improved method of increasing the concentration of endogenous growth hormone in the bloodstream of an economic mammal by administering a synergistic combination of an estrogen and growth hormone releasing factor.

BACKGROUND OF THE INVENTION

An important part of the recent explosion of research in peptide chemistry and the effect of protein hormones on all life forms has been research in growth hormone. The study of the production of growth hormone in various animals has revealed that a relatively small peptide known as growth hormone releasing factor has a major role in the production and secretion of growth hormone in all the species which have been studied. Interestingly, endogenous growth hormone releasing factor (GRF), is a very similar peptide in all of the species whose GRF has been sequenced. It is a peptide of 43 or 44 amino acids in all known species, and the acid terminal of the peptide is amidated in all known species except the rat. The sequence of amino acids in the various endogenous GRF's is quite similar; indeed, bovine GRF is identical to caprine GRF.

The following nomenclature is used in this document. The term "growth hormone releasing factor" (GRF) is used broadly to refer to any peptide which functions to increase the production and release of growth hormone in an economic mammal. The term "endogenous GRF" is used to refer to GRF naturally produced by an animal. In referring to synthetically or recombinantly produced GRF's, an initial is used to indicate the species whose GRF has been duplicated; e.g., "h" for human, "b" for bovine, etc. When a GRF is the acid form, the fact is stated; it is amidated otherwise. The term "analog" is used to refer to peptides which function as GRF's, but have less amino acids than the endogenous GRF, or a different sequence. Synthetic GRF's containing less amino acids than the endogenous GRF are indicated by a number; e.g. "hGRF29" indicates a GRF made up of the first 29 amino acids of human endogenous GRF.

The benefit of increasing the growth hormone level in an economic mammal is now well established. The most conspicuous known benefit is the increase in milk production by a dairy cow when growth hormone is increased. Improved growth rates and feed efficiency by pigs and sheep having increased growth hormone levels have been reported in the literature. The same beneficial effects have not yet been reported in cattle, but it must be realized that growth hormone and GRF are still scarce and expensive, and it is believed that no cattle feeding trials with either agent have yet been done. For some years the growth rate of abnormally small children has been increased by direct administration of growth hormone, at great expense because of the difficulty of obtaining the hormone, and no comparable amount of study has as yet been devoted to the use of growth hormone in economic mammals.

The most extensively studied GRF, of course, is the human. It has been found that the endogenous human GRF peptide can be extensively modified without destroying its effectiveness in increasing the production and secretion of growth hormone. Human GRF analogs of 23 to 40 amino acids have been made, in both the amidated and acid-terminated forms, and found to be active. Further, various changes have been made in the endogenous peptide, such as the interchange of histidine, 3-methylhistidine or N-acetyltyrosine in place of tyrosine at the 1-position of the peptide. Those substances are also effective.

It is perhaps not surprising, in view of the similarity of the endogenous GRF's of different species, that they typically are effective across species. For example, Kraft et al., *Domestic Animal Endocrinology* 2, 133–39 (1985) showed that endogenous human GRF and a human GRF analog having 40 amino acids and a free acid terminal (hGRF40 acid) were active in rats, Rhesus monkeys, rabbits, sheep, cattle and chickens, as well as in humans.

In the human, it appears that GRF is produced both by pancreatic tumors and by the hypothalamus. Identical peptides are produced by both organs. The earliest GRF work was done with peptide produced by human pancreatic tumors, but it has now been clearly shown that the normal pancreas, as well as the hypothalamus, produces the same peptide, which is endogenous human GRF.

There is an extensive literature on GRF and its relationship with the production and secretion of growth hormone. The following articles are mentioned as giving an overview, and an entry into the literature.

Ling et al., *Ann. Rev. Biochem.* 54, 403–23 (1985)
Baird et al., *Neuroendocrinoloqy* 42, 273–76 (1986)
Kensinger et al., *Fed. Proc.* 45, 280 (1986)
Wehrenberg et al., *Endocrinology* 114, 1613–16 (1984)

It has been found that, in many situations, the administration of estrogens to animals also produces an increase in endogenous growth hormone concentration. For example, Frantz et al., *J. Clin. Endocr.* 25, 1470–80 (1965), found that the administration of large doses of diethylstilbestrol to normal men increased growth hormone concentration, measured with the patients fasting. Trenkle, *J. An. Sci.* 31, 389–93 (1970), observed increased growth hormone in steers which were fed a conventional finishing diet with the addition of 10 mg/head/day of stilbestrol.

Ethinyl estradiol or "conjugated estrogens" were administered intravenously to normal men by Wiedemann et al., *J. Clin. Endocr. and Metab.* 42, 942–52 (1976). The authors observed a significant increase in growth hormone in 5 of 6 patients.

Thus, in general, physiologists are aware that the administration of estrogens to animals increases or tends to increase the animals' concentration of growth hormone.

SUMMARY OF THE INVENTION

The present invention provides a synergistic method of increasing the concentration of endogenous growth hormone in the bloodstream of an economic mammal which comprises the simultaneous administration of synergistically effective amounts of an estrogen and a growth hormone releasing factor.

DETAILED DESCRIPTION OF THE INVENTION

This invention provides a significant improvement over the art, in that the present synergistic combination causes the treated animals to produce and secrete markedly higher amounts of growth hormone than one would expect, given the known levels of improvement given by GRF and estrogens.

The invention is of use in economic mammals generally, of which the most highly preferred animal is the dairy cow. Bovines, or cattle, constitute the most preferred class of mammals, and cattle and pigs are also a preferred class. Cattle, pigs and sheep are a third preferred class. The invention is also of use in other economic mammals, including goats, camels, horses and the like, but use in such animals is of less immediate importance.

As was explained above, GRF from one species will increase growth hormone in other species. Accordingly, in practicing this invention, one need not use only GRF of the species being treated. It is preferred to administer GRF of the same species—for example, to administer ovine GRF to sheep. However, the benefit of the invention will be obtained when GRF of any mammalian species is administered to any economic mammal. For example, human GRF may be given to pigs, sheep or cattle, bovine GRF may be given to sheep or pigs, porcine GRF may be given to cattle or sheep, and so forth, according to economic considerations or convenience, with confidence that the benefit of the invention will be obtained.

Of course, GRF isolated from animal organs may be used, but it is much more practical to prepare it synthetically or by recombinant methods. Both synthetic and recombinant production of peptides are now conventional and numerous types of GRF have been prepared thereby. See U.S. Pat. Nos. 4,585,756 and 4,605,643 for a compilation of references on the subject.

It has been shown that not only the complete GRF's, but also many analogs of GRF, are effective to increase the production and release of growth hormone. For example, the 23, 27, 29, 30, 31, 34, 37 and 40-amino acid analogs of human GRF have all been made and found to be effective. However, the first 29 amino acids appear to provide most of the activity. Further, both amidated and acid-terminated analogs and complete GRF's have been shown to be effective.

Accordingly, it is believed to be common knowledge in the art that complete GRF's, and GRF analogs, in both amidated and acid-terminated forms, will increase growth hormone in the homologous species and in other species as well. Thus, in the practice of this invention, the term "growth hormone releasing factor (GRF)" is used to include all mammalian GRF's, and all effective analogs of those GRF's, in both amidated and acid forms. Those of skill in the art know how to recognize effective analogs, and how to titrate the dose of a given type of GRF to obtain the optimum result in a given species.

While any estrogenic substance may be used as the estrogen agent in the present invention, from the standpoint of obtaining efficacy, only those estrogenic substances which can be accepted for administration to food animals can be put into actual use. An estrogenic substance, in the common understanding of physiologists, is a substance which, administered to a normal female animal, will cause growth of the uterus and teats. As all physiologists know, a great many compounds, primarily steroids, are estrogens and are effective in the present invention. See Applezweig, *Steroid Drugs*, McGraw-Hill, Vol. I (1962) and Vol. II (1964) for a comprehensive study of estrogens.

In actual use, however, the acceptable estrogens for food-producing animals are estrone, estradiol and zeranol, and the ester derivatives of those substances. The simple esters, such as the $C_1$–$C_6$ alkanoates, and the benzoates, formed on one or two of the available hydroxy groups of estradiol and zeranol, or on the one hydroxy group of estrone, are established as useful estrogens. For example, estradiol benzoate, estradiol dipropionate, estrone acetate, zeranol hexanoate, zeranol dibutyrate and the like are typical of the agents which may be used as desired as the estrogen agents in the present invention.

The preferred estrogens for use in the present inventions are zeranol and estradiol; estradiol is equally preferred in the basic form or in the form of $C_1$–$C_6$ alkanoates or benzoate. The most preferred specific estrogens are zeranol, estradiol, estradiol benzoate, and estradiol dipropionate.

The present invention is defined as comprising the simultaneous administration of an estrogen and a GRF. By the term "simultaneous" is meant the administration of the two agents in such a manner that both of them are available to the growth hormone-producing and secreting organs at the same time and in adequate amounts to synergistically provide the benefit of the invention. Of course, it is not implied that both agents must be administered precisely together, as by the precisely simultaneous injection of the two agents at once. Rather, the two agents are intended to be administered in any practical manner which provides that both are simultaneously available.

For example, a preferred means of administration is continuously, using dosage forms or dosage devices which pay out the agents in an essentially molecule-by-molecule manner.

Simultaneous administration may be accomplished, however, by many other means. The agents may be administered pulse-wise, for example, by osmotic or mechanical pumps which deliver a measured quantity of the agent at pre-set intervals. Indeed, pulse-wise administration of the GRF is a preferred procedure, because it has been shown that growth hormone secretion is episodic, and accordingly, the pulsed administration of GRF is more efficient than is continuous administration of that agent. Thus, continuous administration of the estrogen, as from a silicone polymer implant, and pulse-wise administration of GRF, is a further preferred embodiment of the invention. Such a method of administration is simultaneous, in the concept of the present invention, because both of the agents are simultaneously present in the animal's system at the time the animal's receptor organs are ready to accept them.

When pulse-wise administration of GRF is used, the timing of the pulses should be frequent enough to increase the number of episodes of growth hormone release above the normal. The frequency is different in different species. In general, however, the frequency of pulse-wise GRF administration should be in the range of about 8–24 pulses per day, more preferably about 12–24 pulses per day. It must be kept in mind that the secretion of growth hormone is affected by the sex and the condition of the animal, and the optimum frequency of GRF pulses may vary from those just stated, under some conditions.

It is preferred to continue the administration of the estrogen and GRF for an economically significantly lengthy period of time. By this phrase is meant administration for a period of time long enough that the economic benefit of increasing growth hormone becomes evident. Most preferably the administration is continued throughout a stage of the treated mammal's life. For example, in the case of dairy cattle, administration would most preferably be continued throughout a period of lactation. In the case of a beef animal or a veal calf, administration would preferably be continued throughout the growing or the finishing stage of the animal's maturation.

Thus, the most preferred period of time for use of the invention is at least about 90 days. Another preferred period of time is at least about 30 days, since, it is believed, that period of time will always be long enough for the effect of increased growth hormone to become evident and create an economic benefit in the treated animal. It is believed that administration should always be continued for at least about 14 days, in order to assure that some benefit of the invention is obtained.

The specific benefit of the invention is described as increased growth hormone in the blood of the treated mammal. It appears that growth hormone does not become effective in the body until it is secreted from the producing glands and circulates in the bloodstream. Thus, the benefit of the present invention is stated in terms of growth hormone in the bloodstream, rather than in terms of the mere production of growth hormone.

The mechanics of administering GRF and estrogen in the practice of the present invention may be accomplished in a number of different ways. Of course, GRF must be administered parenterally in some way, because it cannot be absorbed if administered orally. The estrogen agent may be administered orally if desired, but the oral dose rates are many times greater than the parenteral dose rates. Accordingly, parenteral administration of the estrogen is greatly preferred. The usual oral methods, such as mixing in the feed, orally administered boluses, tablets and liquids and the like, may be used for the estrogen if desired.

Both agents may be diluted to a convenient volume, and injected intravenously, intramuscularly or subcutaneously with a mechanical pump. Such pumps, which were used in the operating examples shown below, are available in a number of different types. All that is necessary is a permanently affixed needle in a convenient location in the animal's body. The same effect is obtained with an implanted battery-driven or chemically-driven pump, which may be permanently installed under the animal's skin.

The two agents need not be administered from the same formulation or device.

A rather convenient slow-release form of GRF can be obtained by preparing a formulation of the peptide in an oil-wax mixture. Similar formulations were taught many years ago, as by U.S. Pat. No. 2,493,202, for the administration of penicillin. Davis et al., *J. Dairy Sci.* 66, 1980-82 (1983), shows the administration of growth hormone to sheep in an oil-wax composition. Such compositions, in general, comprise in the range of 5-10% wax in a vegetable oil. Suitable waxes include carnauba wax, beeswax and the like, and the most commonly used oils are peanut or sesame oil. The concentration of GRF in the formulation, and the amount of formulation to inject, of course, are readily calculated from the desired daily dose of GRF.

Estrogens are very conveniently administered from silicone polymer implantable devices. See, for example, U.S. Pat. No. 4,191,741, which discusses a particularly convenient device for the administration of estradiol.

Both of the agents may be administered in the form of microcapsules. The microencapsulation of drugs and other substances has been the subject of research for many years. The following references are mentioned for the convenience of the reader; veterinary pharmacists will be aware of the following and numerous other references concerning microencapsulation.

Goosen et al. microencapsulated living tissue or cells for implantation, using capsules formed of semi-permeable membranes. Alginates were preferred. U.S. Pat. No. 4,487,758. To much the same effect are the publications of Damon Corporation, such as U.S. Pat. Nos. 4,352,883 and 4,409,331.

Polylactic and polyglycolic acids have been used to form microcapsules. U.S. Pat. No. 4,479,911 and PCT Publication No. 83/03061.

Perhaps the most widely used type of microcapsules are those comprising cellulose esters such as cellulose acetate or butyrate. Typical publications include U.S. Pat. Nos. 3,954,678 and 3,859,228 and British Patent No. 1,297,476.

Recently, diffusion-driven implantable devices for the administration of peptides have been devised, and may conveniently be used for the administration of GRF. See U.S. Pat. No. 4,452,775, which describes a matrix composed of cholesterol with appropriate binding and lubricating agents, and U.S. Pat. No. 4,526,938, which teaches a hydrogel-forming polymer. Such polymeric matrixes may be prepared as taught in those patents, and may be combined with GRF and adjusted according to the usual procedures in the formulations art to obtain the desired dosage range of GRF for the animal to be treated.

Still further, either or both agents may be administered with osmolality-driven pumps. Alza Corporation is particularly noted for constructing such devices. In general, osmolality-driven devices use a semi-permeable membrane to separate a reservoir of active ingredient from the body, and to control the rate of release of active ingredient.

A particularly preferred and convenient method of administering the agents of the present invention is from separate devices. The estrogen agent, in this mode, is administered from an implantable device, which delivers the desired dose of estrogen essentially continuously throughout the life of the device. A silicone polymer device is particularly preferred for delivering the estrogen. The GRF, on the other hand, is administered from a separate implanted pump, or injectable dosage form, such as an oil-wax preparation or a polymerized matrix. The GRF administration may be continuous, or may be episodic as discussed above. When GRF is administered from a mechanical implanted pump, episodic administration is readily obtained from a programmed pump which delivers a pulse at the desired intervals.

The increase of growth hormone, which is the benefit of the present invention, is brought about by administering synergistically effective growth hormone-increasing amounts of estrogen and GRF to the animal. Such amounts are those which, in combination, produce a greater increase in growth hormone than either agent alone can achieve. In general, effective amounts of GRF are in the range from about 0.5 to about 3 mg/day for sheep, goats or pigs, and in the range from about 3 to about 12 mg/day for cattle. The doses and dose ranges are discussed in this document in terms of the daily dose, but the reader must understand that the daily dose is to be administered substantially continuously, or in pulse-wise aliquot doses, throughout the 24 hours. More preferred dose ranges are from about 1 to about 2 mg of GRF per day for sheep, pigs or goats, and from about 4 to about 8 mg/day for cattle. The knowledgeable reader will understand that research in GRF is still intense, and more potent GRF analogs may well be discovered. The preferred doses of more potent analogs, of course, will be smaller than those stated here. The most beneficial dose for a given animal will vary with its size, its state of health and nourishment, whether delivery is continuous or episodic, the desired growth rate or milk yield, and the identity of the GRF to be used. Trivial experiments are used to titrate various GRF dose rates and find the optimum dose per day for the best synergistic effect.

The correct dose of estrogen is in the general range from about 10 to about 500 mcg/day for cattle, and from about 3 to about 150 mcg/day for pigs, goats and sheep. More preferred dose ranges are from about 10 to about 100 mcg/day for cattle, and from about 3 to about 35 mcg/day for pigs, goats and sheep. Still more preferred dose ranges are from about 50 to about 100 mcg/day for cattle, and from about 15 to about 35 mcg/day for pigs, goats and sheep. More generally, the estrogen dose may advantageously be the same as that regularly used when the particular estrogen is administered as an anabolic agent.

The animal scientist will understand, of course, that the optimum dose of GRF and of estrogen for a given group of animals under the existing cultural practices must be experimentally determined, using the fundamental experimental practices of animal husbandry.

The unexpected benefit of the present invention is illustrated by the following operating examples.

EXAMPLE 1

Wethers weighing about 32 kg were confined in metabolism crates for about 7 days before the experiment began. Half of the animals had been implanted with a silicone polymer implant containing estradiol about 25 days before the experiment began. The implant released about 25 mcg/day of estradiol during the experimental period. Two days before the start of the treatment schedule, a Silastic (Dow Corning Corporation) cannula was inserted in each jugular vein of each wether. Four animals, two implanted and two unimplanted, were assigned to three GRF treatments, 1.5 mg/day, 0.33 mg/day and control. The GRF which was used was hGRF in the acid form, synthesized by solid phase synthetic methodology according to the general procedure of Merrifield et al., *Biochemistry* 21, 5020 (1982).

GRF was infused through one of the cannulae continuously for 5 days to the treated wethers, using a Harvard peristaltic pump. The GRF was diluted in physiological saline to a concentration such that the actual delivery rate was 0.5 ml of infusate per minute.

Six blood samples were collected from each wether each day, beginning 1 day before the start of infusion and continuing 1 day after the end of it. Two samples were obtained within 1 hour just before the beginning of each 1-hour ad libitum meal, and 1 sample was taken at the end of each meal. The animals received two 1-hour meals daily at 12 hour intervals. Additional blood samples were taken 1 hour before, just before, 10 minutes after and 60 minutes after the start of infusion. At the end of the infusion period, additional blood samples were obtained at 10, 20, 30 and 60 minutes after the termination of infusion.

The plasma was separated from the other components of the blood samples, and was analyzed for growth hormone by a standard radioimmunological procedure.

The table below reports the growth hormone levels in the animals, reported as means of all of the analyses in the stated time period. The data from animals which were implanted with estradiol are indicated by "+" in the column headed Estradiol.

TABLE I

| Treatment hGRF mg/day | Estradiol | Plasma GH ng/ml | | | | | |
|---|---|---|---|---|---|---|---|
| | | Pre-treatment | Infusion Period (Days) | | | | Post-treatment |
| | | | 1 | 2 | 3 | 4 | 5 | |
| Control | + | 2.8 | 3.3 | 4.3 | 2.9 | 5.2 | 4.2 | 2.4 |
| | − | 9.8 | 10.7 | 12.8 | 11.9 | 9.9 | 5.8 | 9.3 |
| 0.33 | + | 5.2 | 8.9 | 6.9 | 7.3 | 5.7 | 8.5 | 5.5 |
| | − | 5.3 | 8.1 | 10.3 | 11.6 | 7.9 | 8.0 | 3.5 |
| 1.50 | + | 6.2 | 30.4 | 36.3 | 48.9 | 48.5 | 62.2 | 13.3 |
| | − | 9.2 | 20.4 | 30.0 | 29.6 | 24.8 | 25.0 | 6.9 |

EXAMPLE 2

This experiment was carried out substantially according to the scheme of Example 1. In this test, the GRF was a hGRF analog having serine in place of methionine at position 27; the GRF was prepared by recombinant methods. Four rates of hGRF were used, 0.75, 1.5 and 3.0 mg/day, and controls. Four lambs were used at each hGRF rate, half of which were implanted with an estradiol implant as described in Example 1.

The hGRF was infused through a subcutaneous Silastic cannula using an IVAC model 630 pump (IVAC Corporation, San Diego). The hGRF was diluted in physiological saline to provide concentrations such that 48 ml/day of each infusate could be supplied to each animal.

Blood samples were taken from each animal and analyzed as described in Example 1, and the growth hormone analyses are presented in Table II below in the same form used in Example 1.

TABLE II

| Treatment hGRF mg/day | Estradiol | Plasma GH ng/ml | | | | | |
|---|---|---|---|---|---|---|---|
| | | Pre-treatment | Infusion Period (Days) | | | | Post-treatment |
| | | | 1 | 2 | 3 | 4 | 5 | |
| Control | + | 11.6 | 5.9 | 10.0 | 6.2 | 10.2 | 8.8 | 8.7 |
| | − | 3.2 | 5.6 | 9.2 | 7.9 | 7.2 | 9.9 | 5.3 |
| 0.75 | + | 5.8 | 14.0 | 11.4 | 20.6 | 18.4 | 25.4 | 8.3 |
| | − | 7.0 | 11.6 | 10.0 | 12.4 | 16.2 | 10.3 | 4.1 |
| 1.50 | + | 10.4 | 23.4 | 26.5 | 25.1 | 28.1 | 27.8 | 8.4 |
| | − | 10.8 | 15.2 | 20.4 | 15.5 | 19.2 | 19.4 | 4.2 |
| 3.00 | + | 8.6 | 27.0 | 23.2 | 25.2 | 31.8 | 37.2 | 10.7 |
| | − | 7.2 | 15.0 | 17.4 | 27.6 | 28.4 | 30.0 | 8.2 |

What is claimed is:

1. A synergistic method of increasing concentration of endogenous growth hormone in the bloodstream of an economic mammal selected from the group consisting of cattle, pigs, sheep, goats, camels, and horses, which comprises the simultaneous administration of synergistically effective amounts of an estrogen and a growth hormone releasing factor.

2. A method of claim 1 wherein the mammal is a bovine.

3. A method of claim 2 wherein the mammal is a dairy cow.

4. A method of claim 2 wherein the growth hormone releasing factor is bovine growth hormone releasing factor.

5. A method of claim 4 wherein the estrogen is estradiol or a $C_1$-$C_6$ alkanoate or benzoate thereof.

6. A method of claim 2 wherein the estrogen is estradiol or a $C_1$-$C_6$ alkanoate or benzoate thereof.

7. A method of claim 2 wherein the estrogen is zeranol or a $C_1$-$C_6$ alkanoate or benzoate thereof.

8. A method of claim 1 wherein the estrogen is zeranol or estradiol, or a $C_1$-$C_6$ alkanoate or benzoate thereof.

9. A method of claim 1 wherein the mammal is a bovine, a pig or a sheep.

10. A method of claim 1 wherein the mammal is a bovine or a pig.

11. A method of claim 9 wherein the estrogen is estradiol or zeranol or a $C_1$-$C_6$ alkanoate or benzoate thereof.

12. A method of claim 10 wherein the mammal is a pig.

13. A method of claim 12 wherein the growth hormone releasing factor is procine growth hormone releasing factor.

14. A method of claim 13 wherein the estrogen is estradiol or zeranol, or a $C_1$-$C_6$ alkanoate or benzoate thereof.

15. A method of claim 12 wherein the estrogen is estradiol or zeranol, or a $C_1$-$C_6$ alkanoate or benzoate thereof.

* * * * *